United States Patent [19]
Hashimoto et al.

[11] Patent Number: 5,782,768
[45] Date of Patent: Jul. 21, 1998

[54] METHOD OF DISPLAYING ULTRASONIC IMAGE AND APPARATUS FOR ULTRASONIC DIAGNOSIS

[75] Inventors: Hiroshi Hashimoto; Yasuhito Takeuchi; Shigeru Inoue, all of Tokyo, Japan

[73] Assignee: GE Yokogawa Medical Systems, Limited, Tokyo, Japan

[21] Appl. No.: 794,794

[22] Filed: Feb. 4, 1997

[30] Foreign Application Priority Data

Mar. 7, 1996 [JP] Japan .................. 8-050630

[51] Int. Cl.$^6$ .................................................. A61B 8/00
[52] U.S. Cl. ................................. 600/443; 128/916
[58] Field of Search ..................... 600/443, 453, 600/457; 128/916

[56] References Cited

U.S. PATENT DOCUMENTS

| | | | |
|---|---|---|---|
| 4,209,022 | 6/1980 | Dory | 600/457 |
| 4,259,870 | 4/1981 | McLeod et al. | 600/456 X |
| 4,880,010 | 11/1989 | Szilard | 600/457 |
| 5,014,711 | 5/1991 | Nagasaki | 600/443 |
| 5,396,890 | 3/1995 | Weng | 600/443 |
| 5,483,963 | 1/1996 | Butler et al. | 600/453 |
| 5,529,070 | 6/1996 | Augustine et al. | 128/916 X |

*Primary Examiner*—Francis Jaworski
*Attorney, Agent, or Firm*—Moonray Kojima

[57] ABSTRACT

A method of displaying an ultrasonic image and an apparatus for ultrasonic diagnosis of this invention are capable of displaying C-mode ultrasonic image without the need of a probe moving mechanism and a probe movement controller. The linear images produced from the B-mode image data sampled along the scanning planes $P(y1,t1)$–$P(y5,t5)$ and in the constant depth $z1$ are displayed by being arrayed in the order of sampling times $t$ of each linear image.

16 Claims, 11 Drawing Sheets

METHOD OF DISPLAYING ULTRASONIC IMAGE AND APPARATUS FOR ULTRASONIC DIAGNOSIS

BACKGROUND OF THE INVENTION

1. Field of the Invention

The present invention relates to a method of displaying an ultrasonic image and an apparatus for ultrasonic diagnosis. More particularly, the invention relates to a method of displaying an ultrasonic image and an apparatus for ultrasonic diagnosis which are capable of displaying an ultrasonic image of C mode.

2. Description of the Related Art

FIGS. 1A and 1B are a set of diagrams explaining the display of an ultrasonic image of C mode carried out by the conventional ultrasonic diagnostic apparatus.

FIG. 1A shows the sampling of image data in B mode at positions on scanning planes P(y1,t1), P(y2,t2), . . . , P(y5,t5) and in a constant depth z1, with an ultrasonic probe being moved in the y-axis direction. The ultrasonic probe is moved in the y-axis direction which is orthogonal to the scanning planes by a probe moving mechanism under control of a probe movement controller. The subject of imaging is a blood vessel α, which runs in the depth z1 at y-axis positions y1 through y5. Accordingly, a plane which extends through the scanning planes P(y1,t1)–P(y5,t5) in the depth z1 cuts the blood vessel α along the longitudinal direction.

The coordinate system has x axis which is the direction in which numerous sonic beams align as a result of electronical scanning, y axis which is orthogonal to the scanning planes and is the direction of movement of the ultrasonic probe, and z axis which is the depth direction of the subject.

FIG. 1B shows an ultrasonic image C(z1) of C mode resulting from data sampling in the constant depth z1. The image C(z1) has its horizontal direction H and vertical direction V corresponding to the x-axis direction and y-axis direction, respectively, of the scanning planes P. Specifically, the ultrasonic image C(z1) is a set of multiple linear images produced from B-mode image data sampled along the scanning planes P(y1,t1)–P(y5,t5) and in the constant depth z1 and arrayed for display in the order of y-axis positions of the scanning planes.

The ultrasonic image C(z1), in which the blood vessel α appears to be black, exhibits the running state and narrowed portion (angiostenosis) of the blood vessel α. In FIG. 1B and also in the following same kind of figures, ultrasonic images are shown rather solidly relative to the coarse sampling positions y1 to y5 for the sake of the simplicity of explanation.

FIGS. 2A and 2B are another set of diagrams explaining the display of an ultrasonic image in C mode carried out by the conventional apparatus. FIG. 2A shows the sampling of image data in B mode at positions on the scanning planes P(y1,t1), P(y2,t2), . . . , P(y5,t5) and in a constant depth z2, with the ultrasonic probe being moved in the y-axis direction. A blood vessel β runs in the depth z2 in its section between the y-axis positions y1 and y2, while it runs deeper than z2 between the y-axis positions y2 and y5. On this account, a plane which extends through the scanning planes P(y1,t1) and P(y2,t2) in the constant depth z2 cuts the blood vessel β along the longitudinal direction, while it does not cut the blood vessel β when it passes through the scanning planes P(y3,t3)–P(y5,t5).

FIG. 2B shows an ultrasonic image C(z2) of C mode resulting from data sampling in the constant depth z2. The blood vessel β disappears intermittently in its section between y-axis positions y3 and y5 where it runs deeper than z2.

The conventional ultrasonic diagnostic apparatus has the following problems.

(1) The ultrasonic diagnostic apparatus without the provision of a probe moving mechanism and probe movement controller does not recognize the y-axis position, and therefore it cannot display a C-mode ultrasonic image.

(2) A blood vessel running in a variable depth depending on the y-axis position results in a C-mode ultrasonic image which vanishes intermittently (refer to FIGS. 2A and 2B).

(3) More than one blood vessel running in different depths cannot be displayed in C-mode ultrasonic images simultaneously.

SUMMARY OF THE INVENTION

Accordingly, a first object of the present invention is to provide a method of displaying an ultrasonic image and an apparatus for ultrasonic diagnosis which are capable of displaying a C-mode ultrasonic image of a subject without the need of a probe moving mechanism and a probe movement controller.

A second object of the present invention is to provide a method of displaying an ultrasonic image and an apparatus for ultrasonic diagnosis which are capable of displaying without intermittence a C-mode ultrasonic image of even a blood vessel running in a variable depth.

A third object of the present invention is to provide a method of displaying an ultrasonic image and an apparatus for ultrasonic diagnosis which are capable of displaying simultaneously C-mode ultrasonic images of blood vessels running in different depths.

In a first aspect, the present invention resides in a method of displaying an ultrasonic image of a subject by scanning the subject through along a plane with an ultrasonic probe, producing a linear image of a subject portion located in a constant depth, and displaying an array of linear images in the order of imaging times.

The operator moves the ultrasonic probe by hand in the direction (y-axis direction) which is virtually orthogonal to the scanning planes (xz planes), producing linear images of the subject sequentially at positions (y-axis positions) along the probe moving direction (y-axis direction). The produced linear images are displayed by being arrayed in the order of imaging times, i.e., in the order of positions of imaging (y-axis positions) along the probe moving direction, resulting in a C-mode ultrasonic image.

Accordingly, the ultrasonic image display method of the first aspect is capable of displaying a C-mode ultrasonic image of a subject without the need of a probe moving mechanism and probe movement controller.

In a second aspect, the present invention resides in a method of displaying an ultrasonic image of a subject by scanning the subject through along a plane with an ultrasonic probe, producing a linear image of a subject portion located in a variable depth depending on the scanning position, and displaying an array of linear images in the order of imaging times.

The ultrasonic image display method of the second aspect is capable of displaying a C-mode ultrasonic image of a subject without the need of a probe moving mechanism and probe movement controller by the same reason as the method of the first aspect.

Moreover, based on the linear imaging of subject portions located in a variable depth depending on the scanning position, instead of a constant depth, this method is capable of displaying without intermittence a C-mode ultrasonic image of a blood vessel running in a variable depth by the movement of the ultrasonic probe at a small angle with the blood vessel running direction.

In a third aspect, the present invention resides in a method of displaying an ultrasonic image of a subject by scanning the subject through along a plane with an ultrasonic probe, producing such a linear image of a subject portion as it derives from the depth-wise projection of a planar image which represents the subject portion located in a variable depth of a constant range or a varied range dependent on the scanning position, and displaying an array of linear images in the order of imaging times.

The above-mentioned "such a linear image as it derives from the depth-wise projection of a planar image which represents the subject portion located in a variable depth of a certain range" signifies a linear image which is equivalent to a linear image produced by the assessment of a planar image of the subject portion across the depth range in the vertical direction (depth direction) at one horizontal position, selecting the minimum value, maximum value or average value in the depth range for the pixel value of the horizontal position, and repeating these operations for successive horizontal positions.

The ultrasonic image display method of the third aspect is capable of displaying a C-mode ultrasonic image of a subject without the need of a probe moving mechanism and probe movement controller by the same reason as the method of the first aspect.

Moreover, based on such linear imaging as to derive from depth-wise projection of planar images which represent subject portions located in a variable depth of a certain range, instead of a constant depth, this method is capable of displaying without intermittence a C-mode ultrasonic image of a blood vessel running in a variable depth by setting the depth range to cover the range of variable depth of the blood vessel. By setting the depth range to cover the ranges of variable depths of multiple blood vessels, this method is capable of displaying C-mode ultrasonic images of the blood vessels simultaneously.

In a fourth aspect, the present invention resides in a method of displaying an ultrasonic image of a subject by scanning the subject through along a plane with an ultrasonic probe, producing a linear image by converting the power level, which first exceeds a threshold value, of Doppler component of echoes which form the scanning plane into pixel values, and displaying an array of linear images in the order of imaging times.

The ultrasonic image display method of the fourth aspect is capable of displaying a C-mode ultrasonic image of a subject without the need of a probe moving mechanism and probe movement controller by the same reason as the method of the first aspect.

Moreover, based on the linear imaging by converting the power level, which first exceeds the threshold value, of the Doppler component of echoes which form the scanning plane into pixel values, this method is capable of producing an ultrasonic image which resembles a solid-geometric picture of a blood vessel and displaying simultaneously C-mode ultrasonic images of blood vessels running in different depths. This method is also capable of producing an ultrasonic image of only a shallow blood vessel among multiple blood vessels of different depths by sampling only Doppler component of the echoes down to a certain depth.

In a fifth aspect, the present invention resides in a method of displaying an ultrasonic image of a subject by scanning the subject through along a plane with an ultrasonic probe, producing a linear image which represents a subject portion located in a variable depth depending on the scanning position, repeating these operations while moving the ultrasonic probe in the direction virtually orthogonal to the scanning planes, and displaying an array of linear images in the order of imaging times.

Based on the linear imaging of subject portions located in a variable depth depending on the scanning position, instead of a constant depth, this method is capable of displaying without intermittence a C-mode ultrasonic image of a blood vessel running in a variable depth by the movement of the ultrasonic probe at a small angle with the blood vessel running direction.

In a sixth aspect, the present invention resides in a method of displaying an ultrasonic image of a subject by scanning the subject through along a plane with an ultrasonic probe, producing such a linear image of a subject portion as it derives from the depth-wise projection of a planar image which represents the subject portion located in a variable depth of a constant range or a varied range dependent on the scanning position, repeating these operations while moving the ultrasonic probe in the direction virtually orthogonal to the scanning planes, and displaying an array of linear images in the order of positions of the ultrasonic probe.

Based on such linear imaging as to derive from depth-wise projection of planar images which represent subject portions located in a variable depth of a certain range, instead of a constant depth, this method is capable of displaying without intermittence a C-mode ultrasonic image of a blood vessel running in a variable depth by setting the depth range to cover the range of variable depth of the blood vessel. By setting the depth range to cover the ranges of depths of multiple blood vessels, this method is capable of displaying C-mode ultrasonic images of the blood vessels simultaneously.

In a seventh aspect, the present invention resides in a method, which is derived from the method of the fifth or sixth aspect, of displaying an ultrasonic image of a subject by varying the depth or the range of depth of imaging depending on the position of the ultrasonic probe.

By varying the depth or the range of depth of imaging depending on the probe moving position, the ultrasonic image display method of the fifth or sixth aspect is capable of displaying without intermittence a C-mode ultrasonic image of even a blood vessel running in a variable depth and in parallel to the probe moving direction.

In an eighth aspect, the present invention resides in a method of displaying an ultrasonic image of a subject by scanning the subject through along a plane with an ultrasonic probe, producing a linear image which represents a subject portion located in a constant depth, repeating these operations while moving the ultrasonic probe in the direction which is virtually orthogonal to the scanning planes and while at the same time varying the depth of imaging depending on the position of the ultrasonic probe, and displaying an array of linear images in the order of probe positions.

By varying the depth of imaging depending on the probe position, though it constant for each scanning plane, this method is capable of displaying without intermittence a C-mode ultrasonic image of even a blood vessel running in a variable depth and in parallel to the probe moving direction.

In a ninth aspect, the present invention resides in a method of displaying an ultrasonic image of a subject by scanning the subject through along a plane with an ultrasonic probe, producing a linear image by converting the power level, which first exceeds a threshold value, of Doppler component of echoes which form the scanning plane into pixel values, repeating these operations while moving the ultrasonic probe in the direction virtually orthogonal to the scanning planes, and displaying an array of linear images in the order of probe positions.

Based on the linear imaging by converting the power level, which first exceeds the threshold value, of Doppler component of echoes which form the scanning plane into pixel values, this method is capable of producing an ultrasonic image which resembles a solid-geometric picture of a blood vessel and displaying simultaneously C-mode ultrasonic images of blood vessels running in different depths. The method is also capable of producing an ultrasonic image of only a shallow blood vessel among multiple blood vessels of different depths by sampling only Doppler component of the echoes down to a certain depth.

In a tenth aspect, the present invention resides in an apparatus for ultrasonic diagnosis which comprises means for scanning a subject through along a plane with an ultrasonic probe, means for producing at least one of a linear image which represents a subject portion located in a constant depth or a linear image which represents a subject portion located in a variable depth depending on the scanning position, and means for displaying an array of linear images in the order of imaging times.

This apparatus is capable of carrying out properly the ultrasonic image display method of the first or second aspect.

In an eleventh aspect, the present invention resides in an apparatus for ultrasonic diagnosis which comprises means for scanning a subject through along a plane with an ultrasonic probe, means for producing such a linear image of a subject portion as it derives from the depth-wise projection of a planar image which represents the subject portion located in a variable depth of a constant range or a varied range dependent on the scanning position, and means for displaying an array of linear images in the order of imaging times.

This apparatus is capable of carrying out properly the ultrasonic image display method of the third aspect.

In a twelfth aspect, the present invention resides in an apparatus for ultrasonic diagnosis which comprises means for scanning a subject through along a plane with an ultrasonic probe, means for producing a linear image by converting the power level, which first exceeds a threshold value, of Doppler component of echoes which form the scanning plane into pixel values, and means for displaying an array of linear images in the order of imaging times.

This apparatus is capable of carrying out properly the ultrasonic image display method of the fourth aspect.

In a thirteenth aspect, the present invention resides in an apparatus for ultrasonic diagnosis which comprises means for scanning a subject through along a plane with an ultrasonic probe, means for producing a linear image which represents a subject portion located in a variable depth depending on the scanning position, means for detecting the position of the ultrasonic probe which is moved in the direction virtually orthogonal to the scanning planes, and means for displaying an array of linear images in the order of probe positions which correspond to the linear images.

This apparatus is capable of carrying out properly the ultrasonic image display method of the fifth aspect.

In a fourteenth aspect, the present invention resides in an apparatus for ultrasonic diagnosis which comprises means for scanning a subject through along a plane with an ultrasonic probe, means for producing such a linear image of a subject portion as it derives from the depth-wise projection of a planar image which represents the subject portion located in a variable depth of a constant range or a varied range dependent on the scanning position, means for detecting the position of the ultrasonic probe which is moved in the direction virtually orthogonal to the scanning planes, and means for displaying an array of linear images in the order of probe positions which correspond to the linear images.

This apparatus is capable of carrying out properly the ultrasonic image display method of the sixth aspect.

In a fifteenth aspect, the present invention resides in an ultrasonic diagnostic apparatus derived from the apparatus of the thirteenth aspect or fourteenth aspect, wherein the linear imaging means varies the depth or the range of depth of imaging depending on the probe position.

This apparatus is capable of carrying out properly the ultrasonic image display method of the seventh aspect.

In a sixteenth aspect, the present invention resides in an apparatus for ultrasonic diagnosis which comprises means for scanning a subject through along a plane with an ultrasonic probe, means for detecting the position of the ultrasonic probe which is moved in the direction virtually orthogonal to the scanning planes, means for producing a linear image which represents a subject portion located in a constant depth in the scanning direction while varying the depth of imaging depending on the probe position, and means for displaying an array of linear images in the order of probe positions which correspond to the linear images.

This apparatus is capable of carrying out properly the ultrasonic image display method of eighth aspect.

In a seventeenth aspect, the present invention resides in an apparatus for ultrasonic diagnosis which comprises means for scanning a subject through along a plane with an ultrasonic probe, means for producing a linear image by converting the power level, which first exceeds a threshold value, of Doppler component of echoes which form the scanning plane into pixel values, means for detecting the position of the ultrasonic probe which is moved in the direction virtually orthogonal to the scanning planes, and displaying an array of linear images in the order of probe positions which correspond to the linear images.

This apparatus is capable of carrying out properly the ultrasonic image display method of ninth aspect.

Other objects and advantages of the present invention will be apparent from the following description of the preferred embodiments of the invention as illustrated in accompanying drawings.

DESCRIPTION OF THE PREFERRED EMBODIMENTS

Embodiment 1

As shown in the embodiments of FIGS. 3,6,8, and 12, the probe is freely movable manually. In a known manner, the scanning ranges along the x,y,z-axes can be set in a memory in the central processing unit, and when the scanning takes place, the scanned data can be compared with the stored range data for appropriate image display. Also, however, such range registry need not be employed in many cases, since the x,y,z-axes scanning would only be of the subject, and direct scan data imaging in the display can be readily provided. That is to say, the based line or base point can be arbitrarily determined rather than have a pre-set base line or base point. The depth can be measured, for example, from the probe head as base point or measured from the body surface, in which case, as is known, differences in echo signals have to be sensed or cancelled out by averaging.

As shown in the embodiments of FIGS. 15,17,21 and 24, the probe is controlled by a probe movement controller. Thus, the base line or point may be established within the probe movement controller, and the image scan data provided in relation thereto. Of course, in these embodiments also, an arbitrary based line or base point can be employed, as desired. In that case, a range registry can be dispensed with. Also, the depth can be measured from the probe head or the body surface, as desired using the foregoing techniques.

The embodiments all contain a feature which is unique to the invention. The invention takes at least one of the B-mode image data, CF-image data, and PD-mode image data obtained from the scanning and then compares the time or y-axis position to the vertical axis of a planar image at a certaing depth of the subject, and thereby produces the image data which is displayed. The embodiments all utilize the foregoing technique and comprises B-mode processor 3, CF-mode processor 4, PD-mode processor 5, a central processing unit 6(A–I) and a time/vertical axis converter 61(A–D) or y-position/vertical axis converter 60(F–I).

Advantageously, using such system components a constant depth image is displayed without interruption.

Figure 1A:
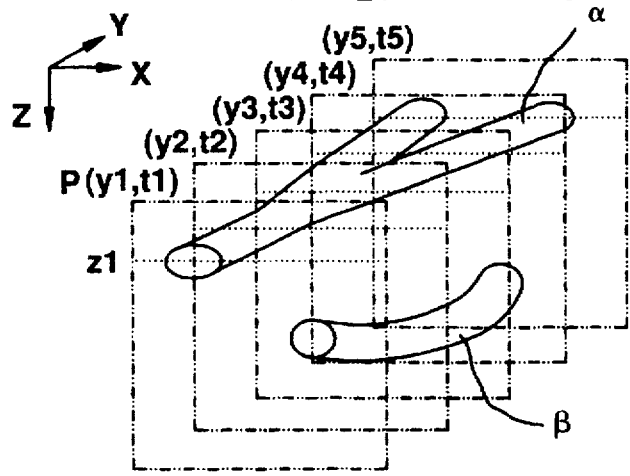
FIGS. 1A and 1B are a first set of diagrams used to explain the display of an ultrasonic image of C mode by the conventional ultrasonic diagnostic apparatus.
Figure 1B:
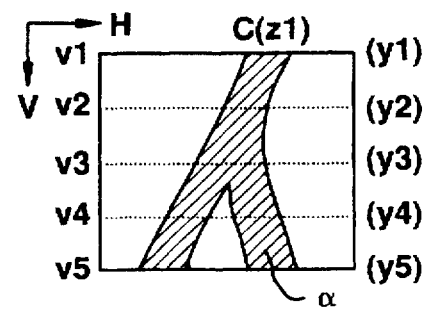
Figure 2A:
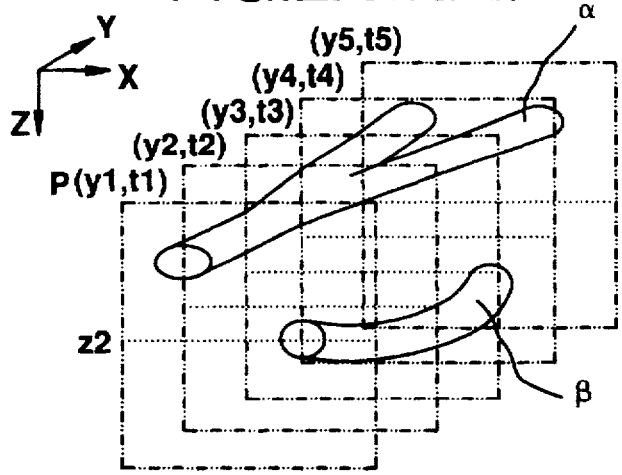
FIGS. 2A and 2B are a second set of diagrams used to explain the display of an ultrasonic image of C mode by the conventional ultrasonic diagnostic apparatus.
Figure 2B:
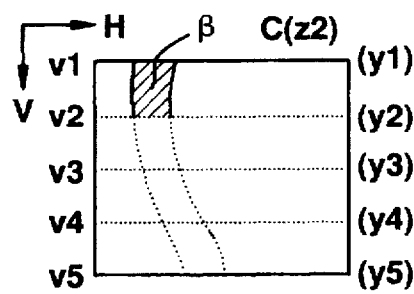
Figure 3:
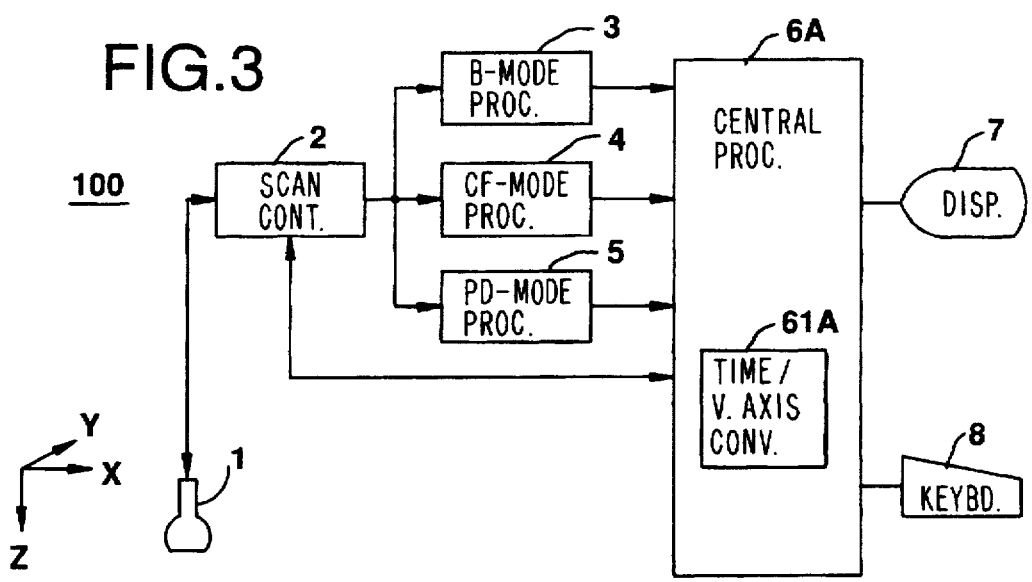
FIG. 3 is a block diagram of the ultrasonic diagnostic apparatus based on a first embodiment of this invention.

FIG. 3 shows in block diagram the ultrasonic diagnostic apparatus based on the first embodiment of this invention.

The ultrasonic diagnostic apparatus 100 includes an ultrasonic probe 1 which emits ultrasonic pulses to a subject of diagnosis and receives ultrasonic echoes from the subject, a scanning controller 2 which implements the electronic scanning of the subject along a plane thereby to sample echo signals, a B-mode processor 3 which produces image data based on the magnitude of ultrasonic echoes, a CF (color flow) mode processor 4 which produces image data based on the phase of Doppler component of the echoes, a PD (power Doppler) mode processor 5 which produces image data based on the power of Doppler component of the echoes, a central processor 6A which produces video data from these image data, a CRT display unit 7 which displays a picture of the video data, and a keyboard 8 which is used by the operator to enter instructions. The central processor 6A includes a time/vertical-axis converter 61A, which will be explained later.

The coordinate system has x axis which is the direction in which numerous sonic beams align as a result of electronical scanning, y axis which is the direction orthogonal to the scanning planes, and z axis which is the depth direction of the subject.

Figure 4A:
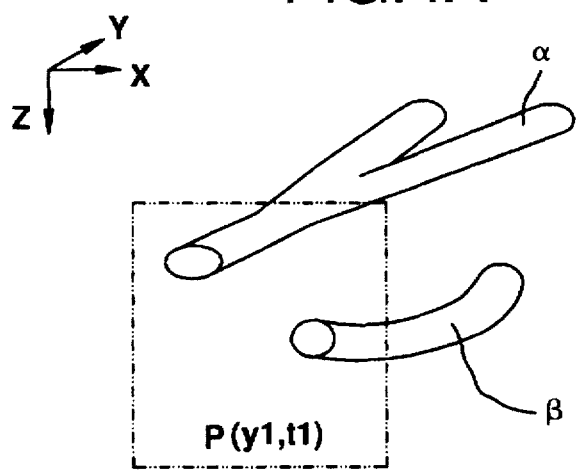
FIGS. 4A and 4B are a set of diagrams used to explain the display of ultrasonic images of B mode by the ultrasonic diagnostic apparatus of FIG. 3.
Figure 4B:
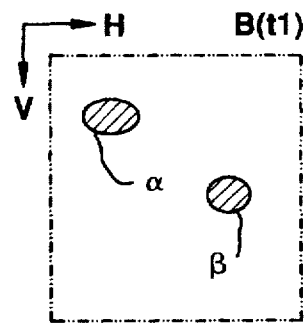

FIGS. 4A and 4B explain the display of B-mode ultrasonic images.

FIG. 4A shows scanning plane P(y1,t1) which is an xz plane scanned at y-axis position y1 at time t1. The scanning plane P(y1,t1) cuts blood vessels $\alpha$ and $\beta$ in their transverse direction.

FIG. 4B shows an ultrasonic image B(t1) resulting from the sampling of B-mode image data along the scanning plane P(y1,t1). The ultrasonic image B(t1) has its horizontal direction H and vertical direction V corresponding to the x-axis direction and z-axis direction, respectively, of the scanning plane P(y1,t1). The blood vessels α and β form black images due to their smaller magnitude of ultrasonic echoes relative to the surrounding portion of tissue.

Figure 5A:
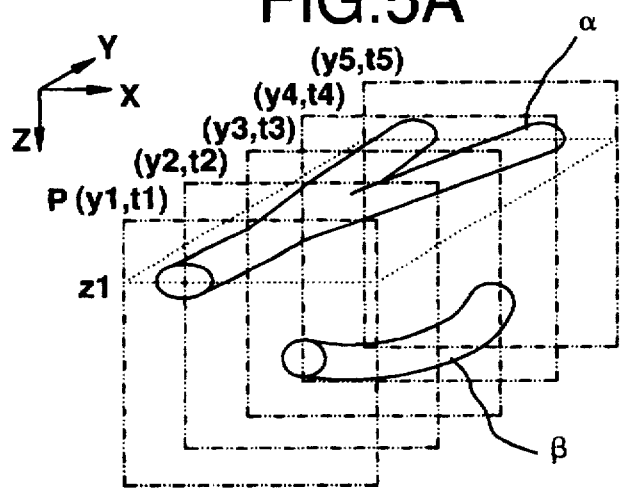
FIGS. 5A and 5B are a set of diagrams used to explain the display of an ultrasonic image of C mode by the ultrasonic diagnostic apparatus of FIG. 3.
Figure 5B:
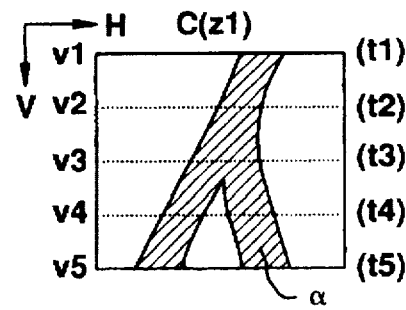

FIGS. 5A and 5B explain the display of a C-mode ultrasonic image.

The ultrasonic diagnostic apparatus 100 is not equipped with a mechanism for moving the ultrasonic probe 1, and therefore the operator moves the probe 1 by hand along the y axis for C-mode imaging. The operator also sets on the keyboard 8 a constant depth z1 which is invariable in the scanning direction.

FIG. 5A shows the sampling of image data in B mode along scanning planes P(y1,t1), P(y2,t2), . . . , P(y5,t5) and in the constant depth z1, with the ultrasonic probe 1 being moved in the y-axis direction. The blood vessel α runs in the depth z1 in the section between the y-axis positions y1 and y5, and accordingly a plane which extends through the scanning planes P(y1,t1)–P(y5,t5) in the depth z1 cuts the blood vessel α in the longitudinal direction.

FIG. 5B shows a C-mode ultrasonic image C(z1) taken in the depth z1. The ultrasonic image C(z1) has its horizontal direction H and vertical direction V corresponding to the x-axis direction and sampling times t, respectively, of the scanning planes P. Specifically, the ultrasonic image C(z1) is a set of linear images produced from the B-mode image data sampled along the scanning planes P(y1,t1)–P(y5,t5) and in the constant depth z1 and arrayed for display in the order of sampling times of the linear images. The C-mode image C(z1), in which the blood vessel α appears to be black, exhibits the running state and narrowed portion of the blood vessel α.

Although in the foregoing explanation, linear images are produced from B-mode image data, linear images may otherwise be produced from CF-mode image data or PD-mode image data.

The time/vertical-axis converter 61A functions to make correspondence between coordinates (h,v) of pixels of the ultrasonic image and pixel values Gz1(n,t) derived from values Sz1(n,t) of echo signals sampled in a constant depth z1 at time points t of scanning planes for sonic beams S(n) aligning in the x-axis direction.

The ultrasonic diagnostic apparatus 100 of the foregoing first embodiment is capable of displaying a C-mode ultrasonic image of a subject without the need of a probe moving mechanism and probe movement controller.

Embodiment 2

Figure 6:
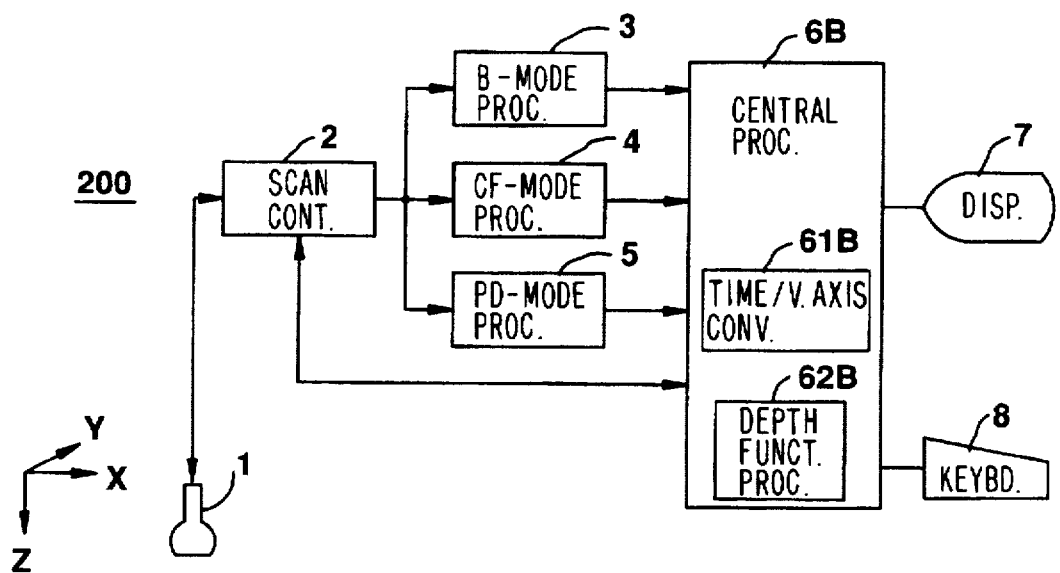
FIG. 6 is a block diagram of the ultrasonic diagnostic apparatus based on a second embodiment of this invention.

FIG. 6 shows in block diagram the ultrasonic diagnostic apparatus based on the second embodiment of this invention.

The ultrasonic diagnostic apparatus 200 includes an ultrasonic probe 1 which emits ultrasonic pulses to a subject of diagnosis and receives ultrasonic echoes from the subject, a scanning controller 2 which implements the electronic scanning of the subject along a plane thereby to sample echo signals, a B-mode processor 3 which produces image data based on the magnitude of ultrasonic echoes, a CF-mode processor 4 which produces image data based on the phase of Doppler component of the echoes, a PD-mode processor 5 which produces image data based on the power of Doppler component of the echoes, a central processor 6B which produces video data from these image data, a CRT display unit 7 which displays a picture of the video data, and a keyboard 8 which is used by the operator to enter instructions. The central processor 6B includes a time/vertical-axis converter 61B and depth-function processor 62B, which will be explained later.

The coordinate system has x axis which is the direction in which numerous sonic beams align as a result of electronical scanning, y axis which is the direction orthogonal to the scanning planes, and z axis which is the depth direction of the subject.

Figure 7A:
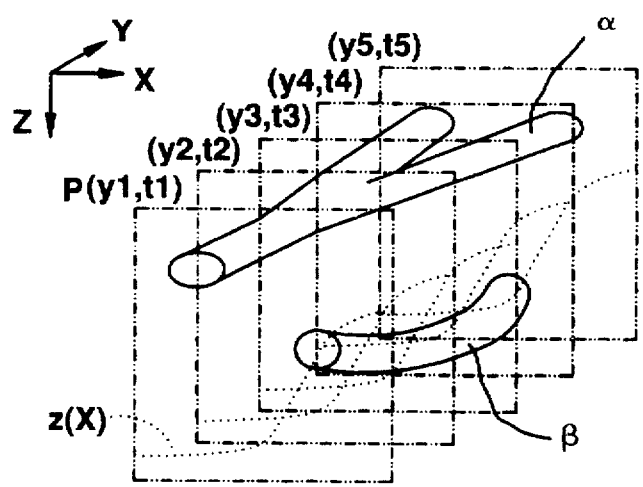
FIGS. 7A and 7B are a set of diagrams used to explain the display of an ultrasonic image of C mode by the ultrasonic diagnostic apparatus of FIG. 6.
Figure 7B:
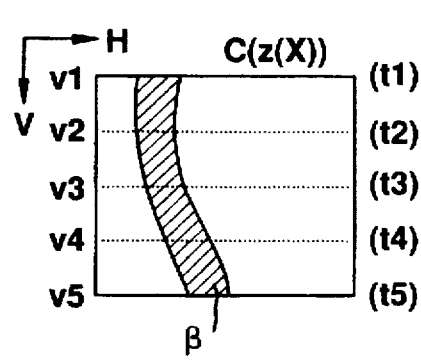

FIGS. 7A and 7B explain the display of a C-mode ultrasonic image.

The ultrasonic diagnostic apparatus 200 is not equipped with a mechanism for moving the ultrasonic probe 1, and therefore the operator moves the probe 1 by hand along the y axis for C-mode imaging. The operator sets in advance for C-mode imaging a depth function z(x), which represents a depth depending on the position in the scanning direction, by drawing a sloped line or curve on the displayed B-mode image by operating the trackball or the like on the keyboard 8.

FIG. 7A shows the sampling of image data in B mode along scanning planes P(y1,t1)–P(y5,t5) and in the variable depth specified in terms of the depth function z(x), with the ultrasonic probe 1 being moved in the y-axis direction. The blood vessel β arches downward in the section between y-axis positions y1 and y5, and at the same time it has a variable x-axis position in this section. The depth function z(x) is set so as to follow the varying depth and x-axis position of the blood vessel β. Consequently, a curving plane which extends through the scanning planes P(y1,t1)–P(y5,t5) along the depth function z(x) cuts the blood vessel β in the longitudinal direction.

FIG. 7B shows an ultrasonic image C(z(x)) of C mode resulting from data sampling along the depth function z(x). The image C(z(x)) has its horizontal direction H and vertical direction V corresponding to the x-axis direction and sampling times t, respectively, of the scanning planes P. Specifically, the ultrasonic image C(z(x)) is a set of multiple linear images produced from B-mode image data sampled along the scanning planes P(y1,t1)–P(y5,t5) and along the depth function z(x) and arrayed for display in the order of sampling times of the linear images. The ultrasonic image C(z(x)), in which the blood vessel β appears to be black in the entire range, exhibits the running state and narrowed portion of the blood vessel β.

Although in the foregoing explanation, linear images are produced from B-mode image data, linear images may otherwise be produced from CF-mode image data or PD-mode image data.

The time/vertical-axis converter 61B functions to make correspondence between coordinates (h,v) of pixels the ultrasonic image and pixel values Gz(x)(n,t) derived from values Sz(x)(n,t) of echo signals sampled along the depth function z(x) at time points t of scanning planes for sonic beams S(n) aligning in the x-axis direction.

The depth-function processor 62B functions to establish a depth function z(x) in response to the operator's setting operation and evaluate the Sz(x)(n,t) values of echo signals in the depth specified by the depth function z(x).

The ultrasonic diagnostic apparatus 200 of the foregoing second embodiment is capable of displaying a C-mode ultrasonic image of a subject without the need of a probe moving mechanism and a probe movement controller. It is also capable of displaying without intermittence a C-mode ultrasonic image of even a blood vessel running in a variable depth.

Embodiment 3

Figure 8:
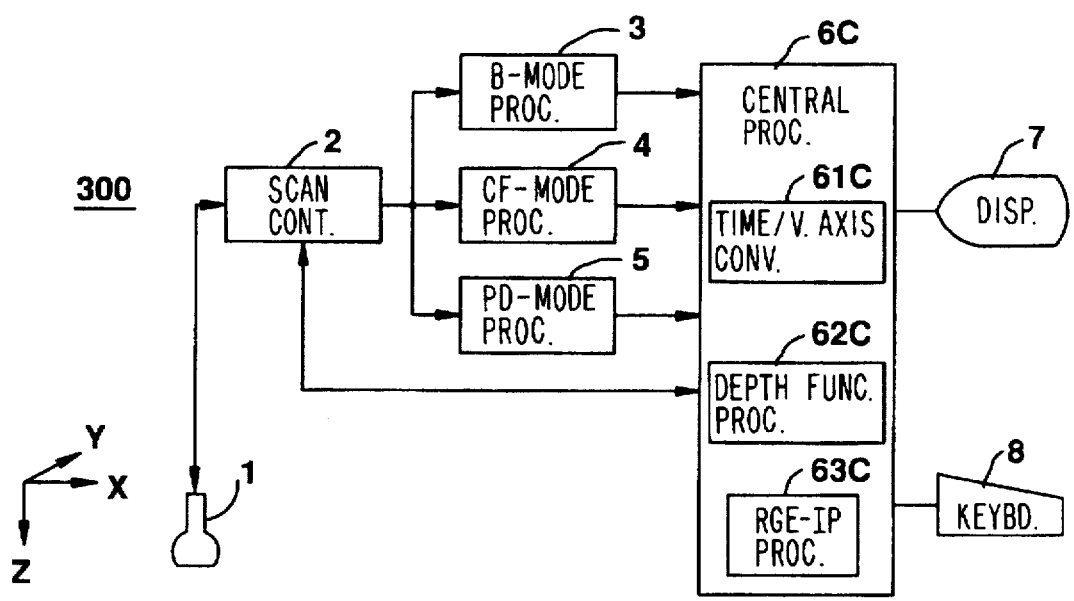
FIG. 8 is a block diagram of the ultrasonic diagnostic apparatus based on a third embodiment of this invention.

FIG. 8 shows in block diagram the ultrasonic diagnostic apparatus based on the third embodiment of this invention. The ultrasonic diagnostic apparatus 300 includes an ultrasonic probe 1 which emits ultrasonic pulses to a subject of diagnosis and receives ultrasonic echoes from the subject, a scanning controller 2 which implements the electronic scanning of the subject along a plane thereby to sample echo signals, a B-mode processor 3 which produces image data based on the magnitude of ultrasonic echoes, a CF-mode processor 4 which produces image data based on the phase of Doppler component of the echoes, a PD-mode processor 5 which produces image data based on the power of Doppler component of the echoes, a central processor 6C which produces video data from these image data, a CRT display unit 7 which displays a picture of the video data, and a keyboard 8 which is used by the operator to enter instructions. The central processor 6C includes a time/vertical-axis converter 61C, depth-function processor 62C and range-IP processor 63C, which will be explained later.

The coordinate system has x axis which is the direction in which numerous sonic beams align as a result of electronical scanning, y axis which is the direction orthogonal to the scanning planes, and z axis which is the depth direction of the subject.

FIGS. 9A and 9B, FIGS. 10A and 10B and FIGS. 11A and 11B explain the display of C-mode ultrasonic images.

The ultrasonic diagnostic apparatus 300 is not equipped with a mechanism for moving the ultrasonic probe 1, and therefore the operator moves the probe 1 by hand along the y axis for C-mode imaging. The operator sets on the keyboard 8 in advance for C-mode imaging either a pair of constant depths za and zb which are invariable in the scanning direction or a pair of depth functions za(x) and zb(x) which represent depths depending on the position in the scanning direction.

Figure 9A:
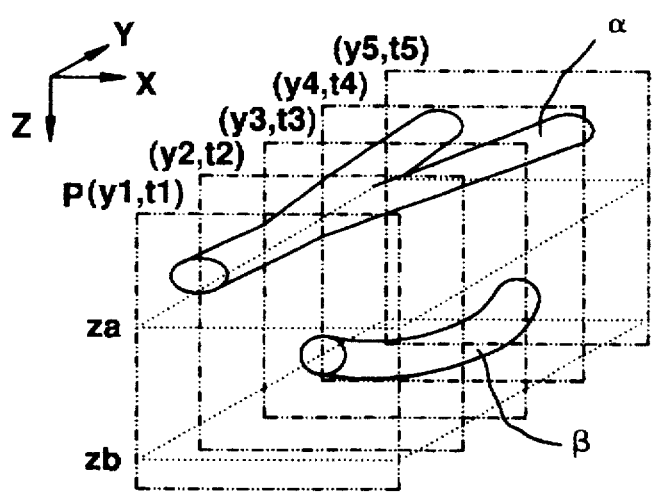
FIGS. 9A and 9B are a first set of diagrams used to explain the display of an ultrasonic image of C mode by the ultrasonic diagnostic apparatus of FIG. 8.

FIG. 9A shows the sampling of image data in B mode along scanning planes P(y1,t1)–P(y5,t5) and in a variable depth within the range defined by the depths za and zb. Although the blood vessel β arches downward in the section between y-axis positions y1 and y5, it is within the specified depth range and therefore image data of the blood vessel β can be sampled without intermittence.

Figure 9B:
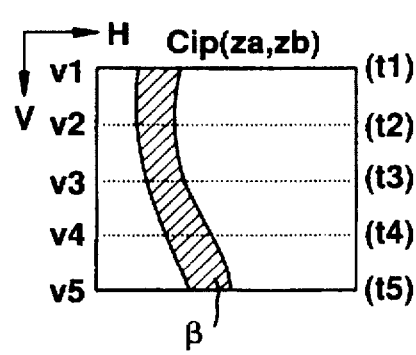

FIG. 9B shows an ultrasonic image Cip(za,zb) of C mode resulting from data sampling in the specified depth range. The image Cip(za,zb) has its horizontal direction H and vertical direction V corresponding to the x-axis direction and sampling times t, respectively, of the scanning planes P. Specifically, the ultrasonic image Cip(za,zb) is a set of multiple linear images produced from B-mode image data sampled along the scanning planes P(y1,t1)–P(y5,t5) and in the specified depth range, rendered the IP (intensity projection) process in the depth direction, and arrayed for display in the order of sampling times of the linear images. The IP process selects image data of the smallest magnitude among the sampled B-mode image data of each sonic beam. The ultrasonic image Cip(za,zb), in which the blood vessel β appears to be black in the entire range, exhibits the running state and narrowed portion of the blood vessel β.

Figure 10A:
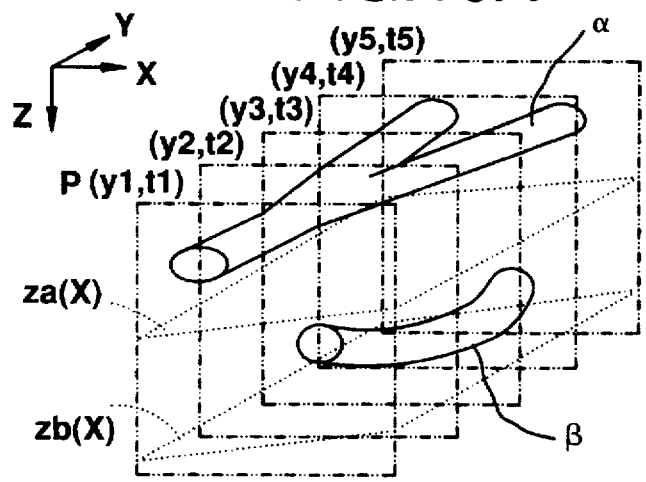
FIGS. 10A and 10B are a second set of diagrams used to explain the display of an ultrasonic image of C mode by the ultrasonic diagnostic apparatus of FIG. 8.

FIG. 10A shows the sampling of image data in B mode along scanning planes P(y1,t1)–P(y5,t5) and in a variable depth within the range defined by the depth functions za(x) and zb(x), with the ultrasonic probe 1 being moved in the y-axis direction. Although the blood vessel β arches downward in the section between y-axis positions y1 and y5, it is within the range of depth functions and therefore image data of the blood vessel β can be sampled without intermittence.

Figure 10B:
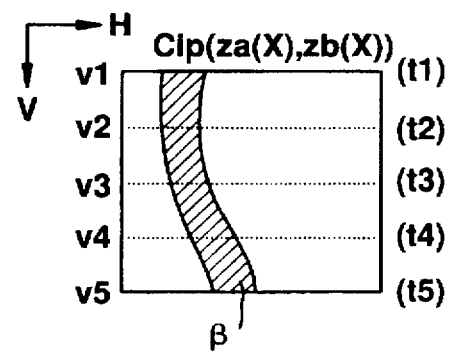

FIG. 10B shows an ultrasonic image Cip(za(x),zb(x)) of C mode resulting from data sampling in the specified depth range. The image Cip(za(x),zb(x)) has its horizontal direction H and vertical direction V corresponding to the x-axis direction and sampling times t, respectively, of the scanning planes P. Specifically, the ultrasonic image Cip(za(x),zb(x)) is a set of multiple linear images produced from B-mode image data sampled along the scanning planes P(y1,t1)–P(y5,t5) and in the specified depth range, rendered the IP process in the depth direction, and arrayed for display in the order of sampling times of the linear images. The ultrasonic image Cip(za(x), zb(x)), in which the blood vessel β appears to be black in the entire range, exhibits the running state and narrowed portion of the blood vessel β.

Figure 11A:
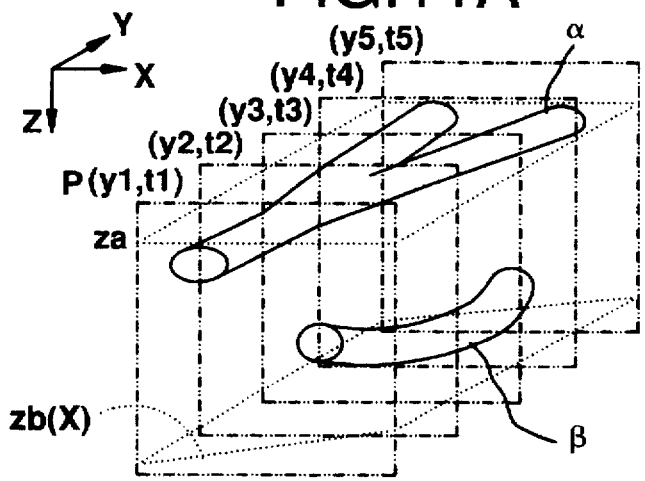
FIGS. 11A and 11B are a third set of diagrams used to explain the display of ultrasonic images of C mode by the ultrasonic diagnostic apparatus of FIG. 8.

FIG. 11A shows the sampling of image data in B mode along scanning planes P(y1,t1)–P(y5,t5) and in a variable depth within the range defined by the constant depth za and the depth function zb(x), with the ultrasonic probe 1 being moved in the y-axis direction. The blood vessels α and β are both within the depth range.

Figure 11B:
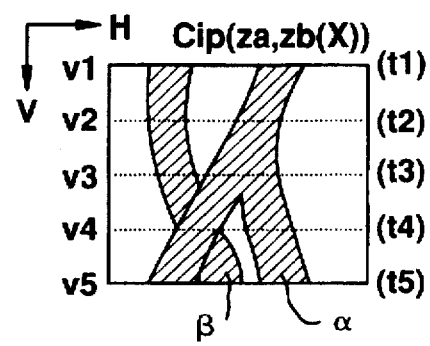

FIG. 11B shows an ultrasonic image Cip(za,zb(x)) of C mode resulting from data sampling in the specified depth range. The image Cip(za,zb(x)) has its horizontal direction H and vertical direction V corresponding to the x-axis direction and sampling times t, respectively, of the scanning planes P. Specifically, the ultrasonic image Cip(za,zb(x)) is a set of multiple linear images produced from B-mode image data sampled along the scanning planes P(y1,t1)–P(y5,t5) and in the specified depth range, rendered the IP process in the depth direction, and arrayed for display in the order of sampling times of the linear images. The ultrasonic image Cip(za,zb(x)), in which the blood vessels α and β appear to be black in the entire range, exhibits the running state and narrowed portion of the blood vessels α and β.

Although in the foregoing explanation, linear images are produced from B-mode image data, linear images may otherwise be produced from CF-mode image data or PD-mode image data.

The time/vertical-axis converter 61C functions to make correspondence between coordinates (h,v) of pixels of the ultrasonic image and pixel values Gip(n,t) derived from IP-processed values Sip(n,t) of echo signals sampled in the specified depth range at time points t of scanning planes for sonic beams S(n) aligning in the x-axis direction.

The depth-function processor 62C functions to establish depth functions za(x) and zb(x) in response to the operator's setting operation.

The range-IP processor 63C functions to evaluate the values Sip(n,t) for B-mode image data based on:

$$Sip(n,t)=\min\{S(n,t,za(x))\sim S(n,t,zb(x))\}$$

where $S(n,t,za(x))\sim S(n,t,zb(x))$ represent signals in the specified depth range of sonic beams S(n) aligning in the x-axis direction sampled at time points t of scanning planes, and min{ } is the function of selecting the minimum value out of the contents of braces.

In the case of PD-mode image data, it evaluates the value Sip(n,t) based on:

$$Sip(n,t)=\max\{S(n,t,za(x))\sim S(n,t,zb(x))\}$$

where max{ } is the function of selecting the maximum value out of the contents of braces.

The ultrasonic diagnostic apparatus 300 of the foregoing third embodiment is capable of displaying a C-mode ultrasonic image of a subject without the need of a probe moving mechanism and probe movement controller. It is also capable of displaying without intermittence a C-mode ultrasonic image of even a blood vessel running in a variable depth, and capable of displaying simultaneously C-mode ultrasonic images of multiple blood vessels running in different depths.

Embodiment 4

Figure 12:
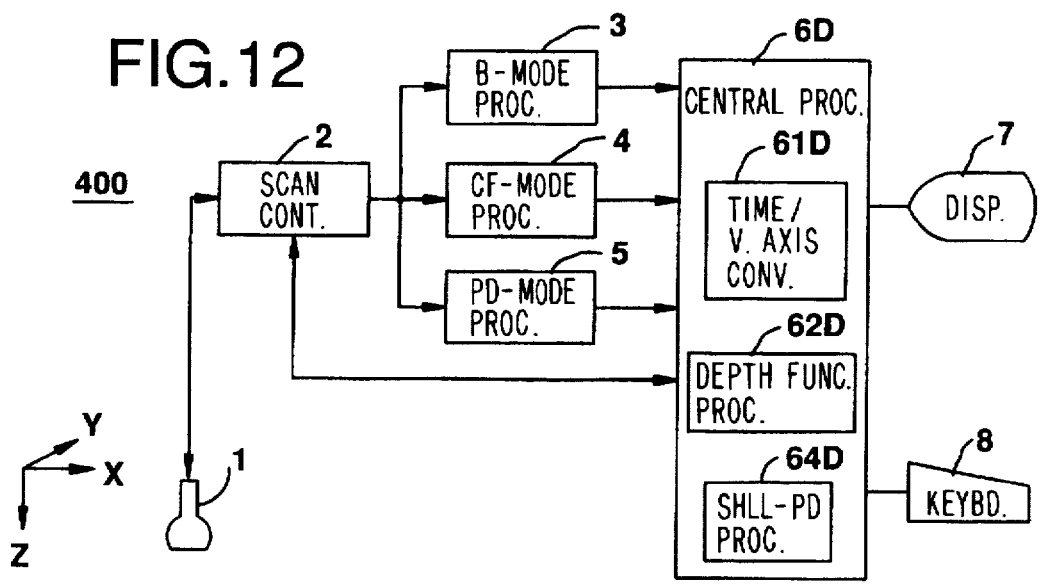
FIG. 12 is a block diagram of the ultrasonic diagnostic apparatus based on a fourth embodiment of this invention.

FIG. 12 shows in block diagram the ultrasonic diagnostic apparatus based on the fourth embodiment of this invention.

The ultrasonic diagnostic apparatus 400 includes an ultrasonic probe 1 which emits ultrasonic pulses to a subject of diagnosis and receives ultrasonic echoes from the subject, a scanning controller 2 which implements the electronic scanning of the subject along a plane thereby to sample echo signals, a B-mode processor 3 which produces image data based on the magnitude of ultrasonic echoes, a CF-mode processor 4 which produces image data based on the phase of Doppler component of the echoes, a PD-mode processor 5 which produces image data based on the power of Doppler component of the echoes, a central processor 6D which produces video data from these image data, a CRT display unit 7 which displays a picture of the video data, and a keyboard 8 which is used by the operator to enter instructions. The central processor 6D includes a time/vertical-axis converter 61D, depth-function processor 62D and shallowest-PD processor 64D, which will be explained later.

The coordinate system has x axis which is the direction in which numerous sonic beams align as a result of electronical scanning, y axis which is the direction orthogonal to the scanning planes, and z axis which is the depth direction of the subject.

FIGS. 13A and 13B and FIGS. 14A and 14B explain the display of C-mode ultrasonic images.

The ultrasonic diagnostic apparatus 400 is not equipped with a mechanism for moving the ultrasonic probe 1, and therefore the operator moves the probe 1 by hand along the y axis for C-mode imaging. The operator sets on the keyboard 8 in advance for C-mode imaging a constant depth zs which is invariable in the scanning direction or a depth function zs(x) which represents a depth depending on the position in the scanning direction, and also sets a threshold value for C-mode imaging.

Figure 13A:
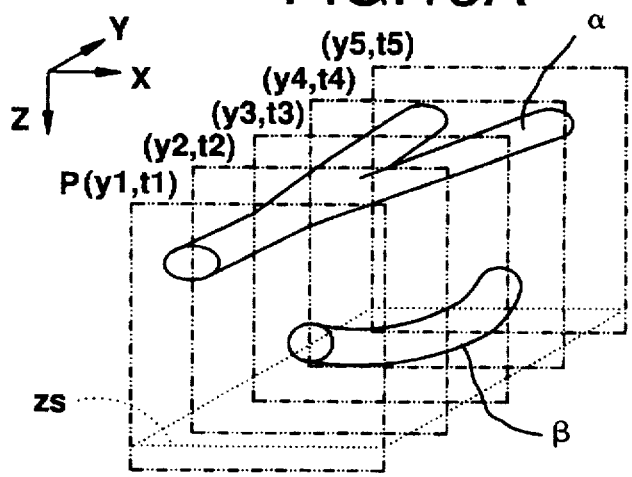
FIGS. 13A and 13B are a first set of diagrams used to explain the display of ultrasonic images of C mode by the ultrasonic diagnostic apparatus of FIG. 12.

FIG. 13A shows the sampling of image data in PD mode along scanning planes P(y1,t1)-P(y5,t5) and in a variable depth within the range down to the constant depth zs, with the ultrasonic probe 1 being moved in the y-axis direction.

Figure 13B:
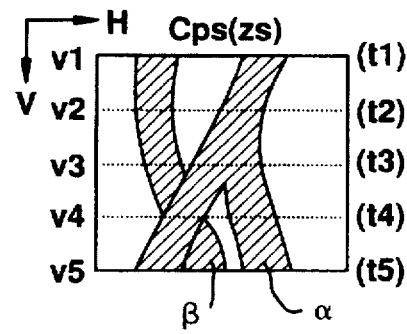

FIG. 13B shows an ultrasonic image Cps(zs) of C mode resulting from data sampling in the specified depth range. The image Cps(zs) has its horizontal direction H and vertical direction V corresponding to the x-axis direction and sampling times t, respectively, of the scanning planes P. Specifically, the ultrasonic image Cps(zs) is a set of multiple linear images produced from image data that has first exceeded the threshold value among the PD-mode image data sampled along the scanning planes P(y1,t1)-P(y5,t5) and in the specified depth range and arrayed for display in the order of sampling times of the linear images. The ultrasonic image Cps(zs), which resembles a solid-geometric picture of the blood vessels α and β, exhibits the running state and narrowed portion of the blood vessels α and β.

Figure 14A:
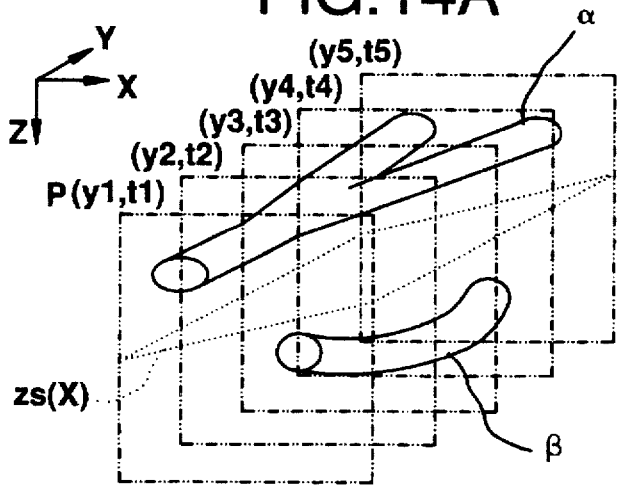
FIGS. 14A and 14B are a second set of diagrams used to explain the display of an ultrasonic image of C mode by the ultrasonic diagnostic apparatus of FIG. 12.

FIG. 14A shows the sampling of image data in PD mode along scanning planes P(y1,t1)-P(y5,t5) and in a variable depth within the range down to the variable depth specified in terms of the depth function zs(x), with the ultrasonic probe 1 being moved in the y-axis direction. The blood vessel α is included within the depth range, while the blood vessel β is not.

Figure 14B:
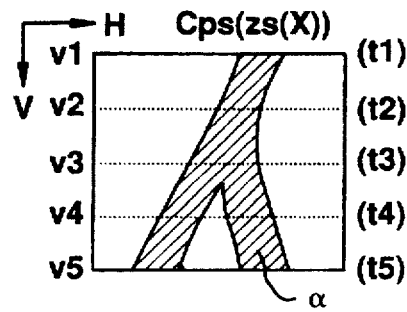

FIG. 14B shows an ultrasonic image Cps(zs(x)) of C mode resulting from data sampling in the specified depth range. The image Cps(zs(x)) has its horizontal direction H and vertical direction V corresponding to the x-axis direction and sampling times t, respectively, of the scanning planes P. Specifically, the ultrasonic image Cps(zs(x)) is a set of multiple linear images produced from image data that has first exceeded the threshold value among the PD-mode image data sampled along the scanning planes P(y1,t1)-P(y5,t5) and in the specified depth range and arrayed for display in the order of sampling times of the linear images. The ultrasonic image Cps(zs), which resembles a solid-geometric picture of only the blood vessel α, exhibits the running state and narrowed portion of the blood vessel α.

The time/vertical-axis converter 61D functions to make correspondence between coordinates (h,v) of pixels of the ultrasonic image and pixel values Gps(n,t) derived from PD data that has first exceeded the threshold value among PD data Sps(n,t) sampled in a specified depth range at time points t of scanning planes for sonic beams S(n) aligning in the x-axis direction. The depth-function processor 62D functions to establish a depth function zs(x) in response to the operator's setting operation.

In the case of setting only a constant depth zs without including a depth function zs(x), the depth-function processor 62D can be eliminated.

The shallowest-PD processor 64D functions to evaluate the value Sps(n,t) based on:

$$Sps(n,t) = shlw\{Spd(n,t,0) \sim Spd(n,t,zs(x)), \theta\}$$

where $Spd(n,t,0) \sim Spd(n,t,zs(x))$ represent PD data in the specified depth range of sonic beams S(n) aligning in the x-axis direction sampled at time points t of scanning planes, and shlw{ } is the function of selecting PD data having shallowest value that exceeds the threshold value $\theta$ out of the contents of braces.

The ultrasonic diagnostic apparatus 400 of the foregoing fourth embodiment is capable of displaying a C-mode ultrasonic image of a subject without the need of a probe moving mechanism and probe movement controller. It is also capable of displaying without intermittence a C-mode ultrasonic image of even a blood vessel running in a variable depth, and capable of displaying simultaneously C-mode ultrasonic images of multiple blood vessels running in different depths.

Embodiment 5

Figure 15:
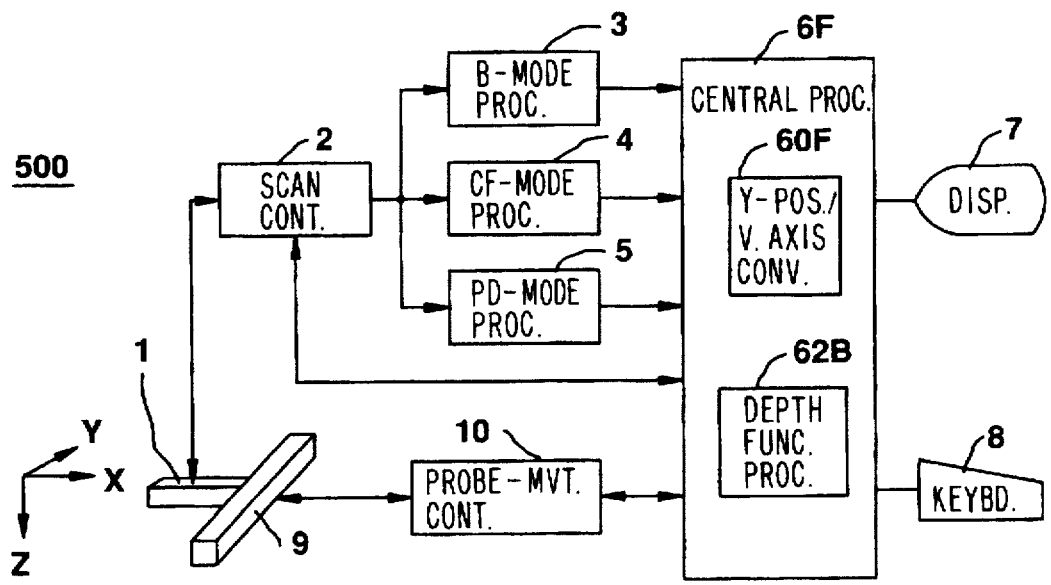
FIG. 15 is a block diagram of the ultrasonic diagnostic apparatus based on a fifth embodiment of this invention.

FIG. 15 shows in block diagram the ultrasonic diagnostic apparatus based on the fifth embodiment of this invention. The ultrasonic diagnostic apparatus 500 includes an ultrasonic probe 1 which emits ultrasonic pulses to a subject of diagnosis and receives ultrasonic echoes from the subject, a scanning controller 2 which implements the electronic scanning of the subject along a plane thereby to sample echo signals, a B-mode processor 3 which produces image data based on the magnitude of ultrasonic echoes, a CF-mode processor 4 which produces image data based on the phase of Doppler component of the echoes, a PD-mode processor 5 which produces image data based on the power of Doppler component of the echoes, a central processor 6F which produces video data from these image data, a CRT display unit 7 which displays a picture of the video data, a keyboard 8 which is used by the operator to enter instructions, a probe moving mechanism 9 which moves the ultrasonic probe 1 in the direction orthogonal to the scanning planes, and a probe movement controller 10 which controls the movement of the ultrasonic probe 1.

The central processor 6F includes a y-position/vertical-axis converter 60F and depth-function processor 62B, which will be explained later.

The coordinate system has x axis which is the direction in which numerous sonic beams align as a result of electronical scanning, y axis which is the direction orthogonal to the scanning planes, and z axis which is the depth direction of the subject.

Figure 16A:
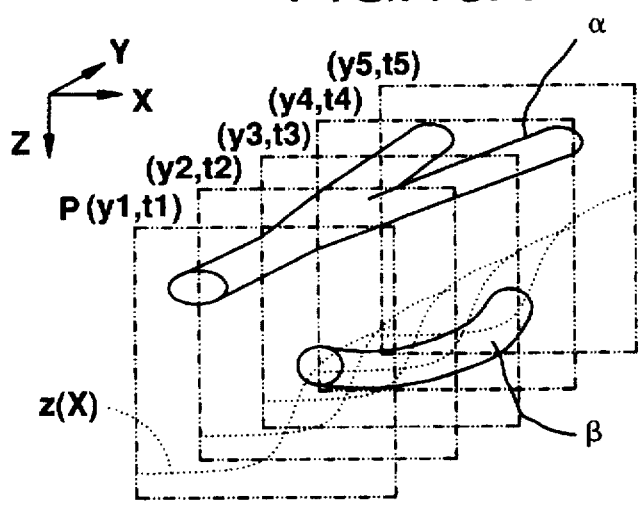
FIGS. 16A and 16B are a set of diagrams used to explain the display of an ultrasonic image of C mode by the ultrasonic diagnostic apparatus of FIG. 15.
Figure 16B:
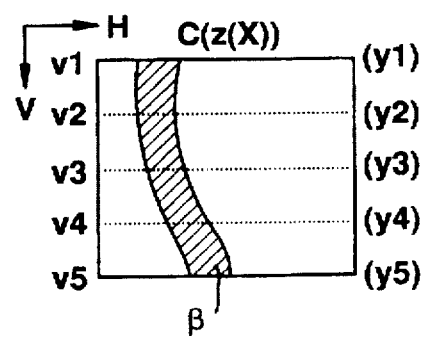

FIGS. 16A and 16B explain the display of a C-mode ultrasonic image.

The operator sets on the keyboard 8 in advance for C-mode imaging a depth function z(x) which represents a depth depending on the position in the scanning direction.

FIG. 16A shows the sampling of image data in B mode along scanning planes P(y1,t1)–P(y5,t5) and in the variable depth specified in terms of the depth function z(x), with the ultrasonic probe 1 being moved in the y-axis direction. The blood vessel β arches downward in the section between y-axis positions y1 and y5, and at the same time it has a variable x-axis position in this section. The depth function z(x) is set so as to follow the varying depth and x-axis position of the blood vessel β. Consequently, a curving plane which extends through the scanning planes P(y1,t1)–P(y5,t5) along the depth function z(x) cuts the blood vessel β in the longitudinal direction.

FIG. 16B shows an ultrasonic image C(z(x)) of C mode resulting from data sampling along the depth function z(x). The image C(z(x)) has its horizontal direction H and vertical direction V corresponding to the x-axis direction and y-axis positions, respectively, of the scanning planes P. Specifically, the ultrasonic image C(z(x)) is a set of multiple linear images produced from B-mode image data sampled along the scanning planes P(y1,t1)–P(y5,t5) and along the depth function z(x) and arrayed for display in the order of y-axis positions of the linear images. The ultrasonic image C(z(x)), in which the blood vessel β appears to be black in the entire range, exhibits the running state and narrowed portion of the blood vessel β.

Although in the foregoing explanation, linear images are produced from B-mode image data, linear images may otherwise be produced from CF-mode image data or PD-mode image data.

The y-position/vertical-axis converter 60F functions to make correspondence between coordinates (h,v) of pixels of the ultrasonic image and pixel values Gz(x)(n,y) derived from values Sz(x)(n,y) of echo signals sampled along the depth function z(x) and at y-axis positions y of scanning planes for sonic beams S(n) aligning in the x-axis direction. The depth-function processor 62B functions to establish a depth function z(x) in response to the operator's setting operation and evaluate the Sz(x)(n,y) values of echo signals in the depth given by the depth function z(x).

The ultrasonic diagnostic apparatus 500 of the foregoing fifth embodiment is capable of displaying without intermittence a C-mode ultrasonic image of even a blood vessel running in a variable depth.

Embodiment 6

Figure 17:
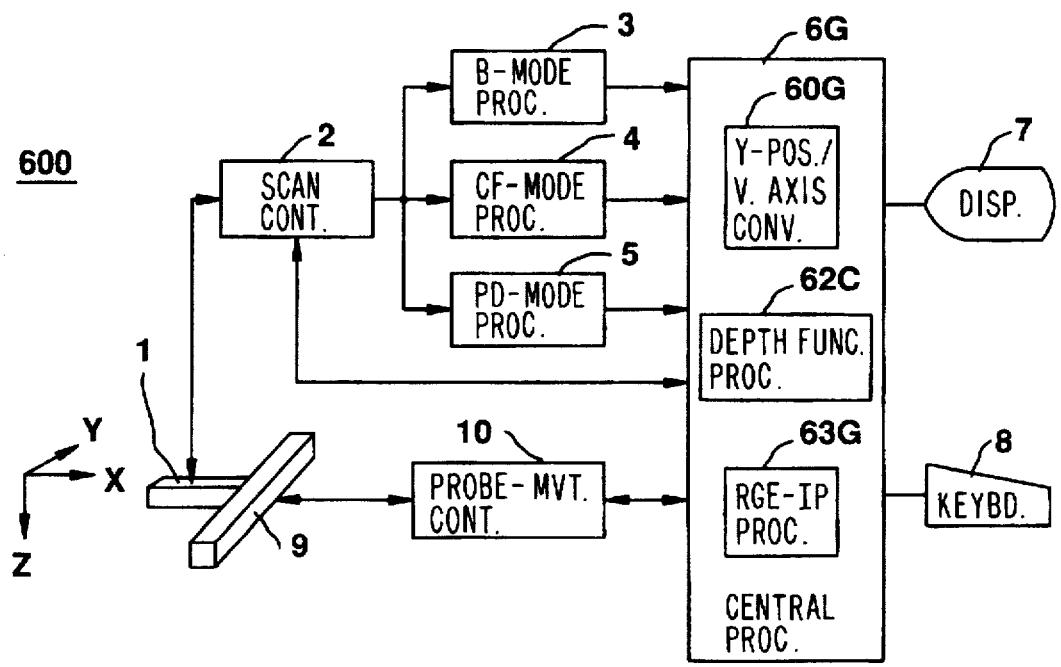
FIG. 17 is a block diagram of the ultrasonic diagnostic apparatus based on a sixth embodiment of this invention.

FIG. 17 shows in block diagram the ultrasonic diagnostic apparatus based on the sixth embodiment of this invention. The ultrasonic diagnostic apparatus 600 includes an ultrasonic probe 1 which emits ultrasonic pulses to a subject of diagnosis and receives ultrasonic echoes from the subject, a scanning controller 2 which implements the electronic scanning of the subject along a plane thereby to sample echo signals, a B-mode processor 3 which produces image data based on the magnitude of ultrasonic echoes, a CF-mode processor 4 which produces image data based on the phase of Doppler component of the echoes, a PD-mode processor 5 which produces image data based on the power of Doppler component of the echoes, a central processor 6G which produces video data from these image data, a CRT display unit 7 which displays a picture of the video data, a keyboard 8 which is used by the operator to enter instructions, a probe moving mechanism 9 which moves the ultrasonic probe in the direction orthogonal to the scanning planes, and a probe movement controller 10 which controls the movement of the ultrasonic probe 1.

The central processor 6G includes a y-position/vertical-axis converter 60G, depth-function processor 62C, and range-IP processor 63G, which will be explained later.

The coordinate system has x axis which is the direction in which numerous sonic beams align as a result of electronical scanning, y axis which is the direction orthogonal to the scanning planes, and z axis which is the depth direction of the subject.

FIGS. 18A and 18B, FIGS. 19A and 19B and FIGS. 20A and 20B explain the display of C-mode ultrasonic images.

The operator sets on the keyboard 8 in advance for C-mode imaging either a pair of constant depths za and zb which are invariable in the scanning direction or a pair of depth functions za(x) and zb(x) which represent depths depending on the position in the scanning direction.

Figure 18A:
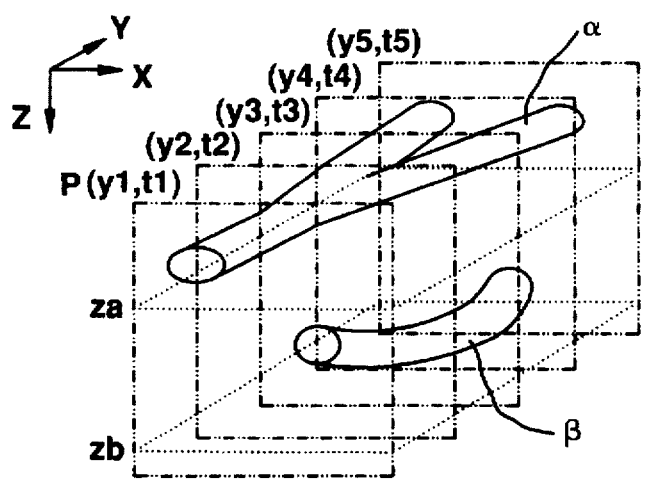
FIGS. 18A and 18B are a first set of diagrams used to explain the display of an ultrasonic image of C mode by the ultrasonic diagnostic apparatus of FIG. 17.

FIG. 18A shows the sampling of image data in B mode along scanning planes P(y1,t1)–P(y5,t5) and in a variable depth within the range defined by the depths za and zb, with the ultrasonic probe 1 being moved in the y-axis direction. Although the blood vessel β arches downward in the section between y-axis positions y1 and y5, it is within the specified depth range and therefore image data of the blood vessel β can be sampled without intermittence.

Figure 18B:
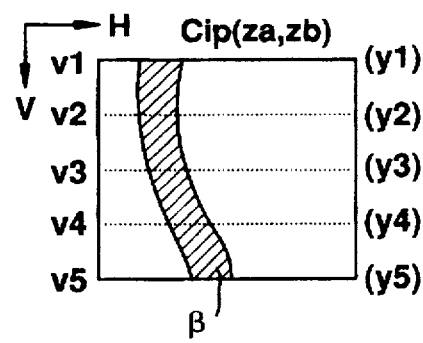

FIG. 18B shows an ultrasonic image Cip(za,zb) of C mode resulting from data sampling in the specified depth range. The image Cip(za,zb) has its horizontal direction H and vertical direction V corresponding to the x-axis direction and y-axis positions, respectively, of the scanning planes P. Specifically, the ultrasonic image Cip(za,zb) is a set of multiple linear images produced from B-mode image data sampled along the scanning planes P(y1,t1)–P(y5,t5) and in the specified depth range, rendered the IP process in the depth direction, and arrayed for display in the order of y-axis positions of the linear images. The IP process selects image data of the smallest magnitude among the sampled B-mode image data of each sonic beam. The ultrasonic image Cip(za,zb), in which the blood vessel β appears to be black in the entire range, exhibits the running state and narrowed portion of the blood vessel β.

Figure 19A:
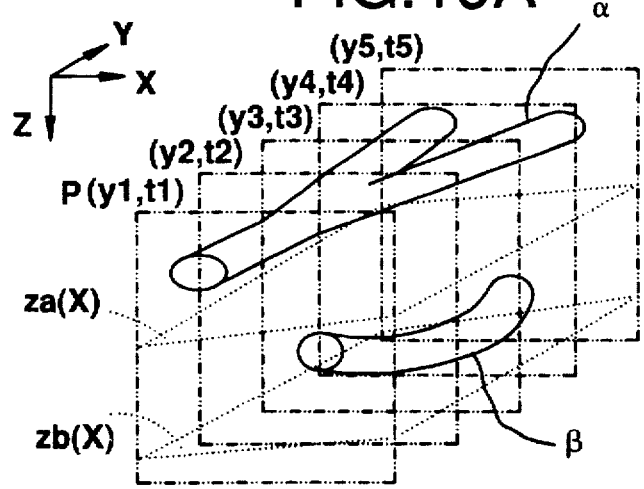
FIGS. 19A and 19B are a second set of diagrams used to explain the display of an ultrasonic image of C mode by the ultrasonic diagnostic apparatus of FIG. 17.

FIG. 19A shows the sampling of image data in B mode along scanning planes P(y1,t1)–P(y5,t5) and in a variable depth within the range defined by the depth functions za(x) and zb(x), with the ultrasonic probe 1 being moved in the y-axis direction. Although the blood vessel β arches downward in the section between y-axis positions y1 and y5, it is within the range of depth functions and therefore image data of the blood vessel β can be sampled without intermittence.

Figure 19B:
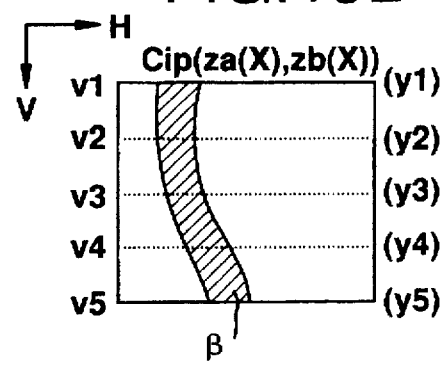

FIG. 19B shows an ultrasonic image Cip(za(x),zb(x)) of C mode resulting from data sampling in the specified depth range. The image Cip(za(x),zb(x)) has its horizontal direction H and vertical direction V corresponding to the x-axis direction and y-axis positions, respectively, of the scanning planes P. Specifically, the ultrasonic image Cip(za(x),zb(x)) is a set of multiple linear images produced from B-mode image data sampled along the scanning planes P(y1,t1)–P(y5,t5) and in the specified depth range, rendered the IP process in the depth direction, and arrayed for display in the order of y-axis positions of the linear images. The ultrasonic image Cip(za(x), zb(x)), in which the blood vessel β appears to be black in the entire range, exhibits the running state and narrowed portion of the blood vessel β.

Figure 20A:
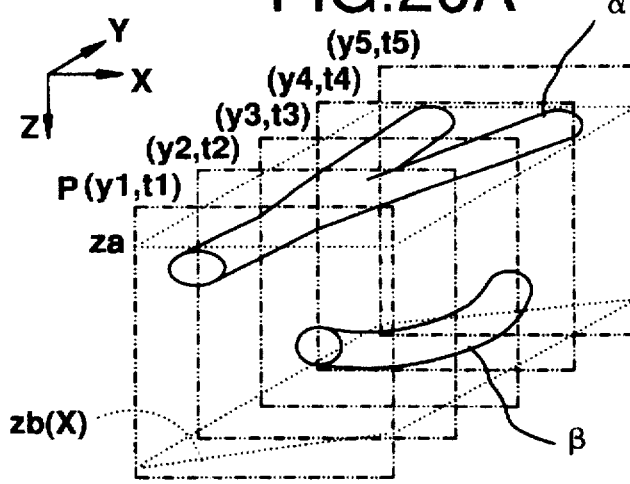
FIGS. 20A and 20B are a third set of diagrams used to explain the display of ultrasonic images of C mode by the ultrasonic diagnostic apparatus of FIG. 17.

FIG. 20A shows the sampling of image data in B mode along scanning planes P(y1,t1)–P(y5,t5) and in a variable depth within the range defined by the constant depth za and the depth function zb(x), with the ultrasonic probe 1 being moved in the y-axis direction. The blood vessels α and β are both within the depth range.

Figure 20B:
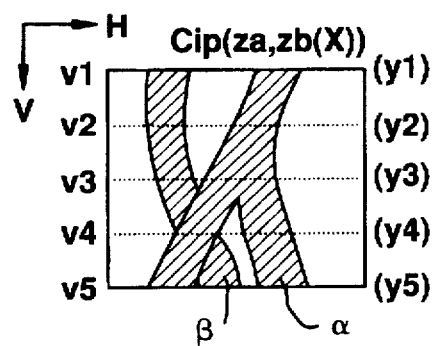

FIG. 20B shows an ultrasonic image Cip(za,zb(x)) of C mode resulting from data sampling in the specified depth range. The image Cip(za,zb(x)) has its horizontal direction H and vertical direction V corresponding to the x-axis direction and y-axis positions, respectively, of the scanning planes P. Specifically, the ultrasonic image Cip(za,zb(x)) is a set of multiple linear images produced from B-mode image data sampled along the scanning planes P(y1,t1)~P(y5,t5) and in the specified depth range, rendered the IP process in the depth direction, and arrayed for display in the order of y-axis positions of the linear images. The ultrasonic image Cip(za,zb(x)), in which the blood vessels α and β appear to be black in the entire range, exhibits the running state and narrowed portion of the blood vessels α and β.

Although in the foregoing explanation, linear images are produced from B-mode image data, linear images may otherwise be produced from CF-mode image data or PD-mode image data.

The y-position/vertical-axis converter 60G functions to make correspondence between coordinates (h,v) of pixels of the ultrasonic image and pixel values Gip(x)(n,y) derived from IP-processed values Sip(x)(n,y) of echo signals sampled in the specified depth range at y-axis positions y of scanning planes for sonic beams S(n) aligning in the x-axis direction.

The depth-function processor 62C functions to establish depth functions za(x) and zb(x) in response to the operator's setting operation.

The range-IP processor 63G functions to evaluate the values Sip(n,y) for B-mode image data based on:

$$Sip(n,y)=min\{S(n,y,za(x))\text{~}S(n,y,zb(x))\}$$

where S(n,y,za(x))~S(n,y,zb(x)) represent signals in the specified depth range of sonic beams S(n) aligning in the x-axis direction sampled at y-axis position of scanning planes, and min{ } is the function of selecting the minimum value out of the contents of braces.

In the case of PD-mode image data, it evaluates the value Sip(n,t) based on:

$$Sip(n,t)=max\{S(n,t,za(x))\text{~}S(n,t,zb(x))\}$$

where max{ } is the function of selecting the maximum value out of the contents of braces.

The ultrasonic diagnostic apparatus 600 of the foregoing sixth embodiment is capable of displaying without intermittence a C-mode ultrasonic image of even a blood vessel running in a variable depth, and capable of displaying simultaneously C-mode ultrasonic images of multiple blood vessels running in different depths.

Embodiment 7

Figure 21:
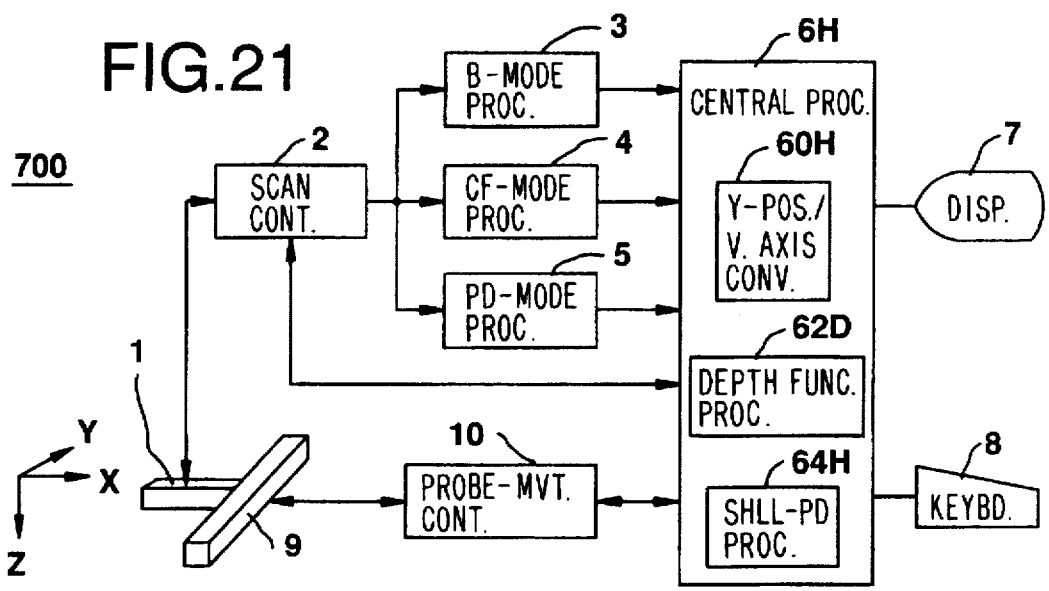
FIG. 21 is a block diagram of the ultrasonic diagnostic apparatus based on a seventh embodiment of this invention.

FIG. 21 shows in block diagram the ultrasonic diagnostic apparatus based on the seventh embodiment of this invention. The ultrasonic diagnostic apparatus 700 includes an ultrasonic probe 1 which emits ultrasonic pulses to a subject of diagnosis and receives ultrasonic echoes from the subject, a scanning controller 2 which implements the electronic scanning of the subject along a plane thereby to sample echo signals, a B-mode processor 3 which produces image data based on the magnitude of ultrasonic echoes, a CF-mode processor 4 which produces image data based on the phase of Doppler component of the echoes, a PD-mode processor 5 which produces image data based on the power of Doppler component of the echoes, a central processor 6H which produces video data from these image data, a CRT display unit 7 which displays a picture of the video data, a keyboard 8 which is used by the operator to enter instructions, a probe moving mechanism 9 which moves the ultrasonic probe 1 in the direction orthogonal to the scanning planes, and a probe movement controller 10 which controls the movement of the ultrasonic probe 1.

The central processor 6H includes a y-position/vertical-axis converter 60H, depth-function processor 62D, and shallowest-PD processor 64H, which will be explained later.

The coordinate system has x axis which is the direction in which numerous sonic beams align as a result of electronical scanning, y axis which is the direction orthogonal to the scanning planes, and z axis which is the depth direction of the subject.

FIGS. 22A and 22B and FIGS. 23A and 23B explain the display of C-mode ultrasonic images.

The operator sets on the keyboard 8 in advance for C-mode imaging a constant depth zs which is invariable in the scanning direction or or a depth function zs(x) which represents a depth depending on the position in the scanning direction, and also sets a threshold value for C-mode imaging.

Figure 22A:
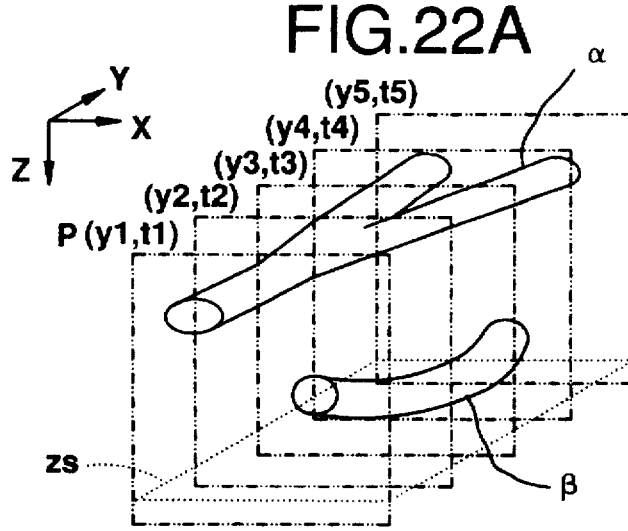
FIGS. 22A and 22B are a first set of diagrams used to explain the display of ultrasonic images of C mode by the ultrasonic diagnostic apparatus of FIG. 21.

FIG. 22A shows the sampling of image data in B mode along scanning planes P(y1,t1)~P(y5,t5) and in a variable depth within the range down to the depth zs, with the ultrasonic probe 1 being moved in the y-axis direction.

Figure 22B:
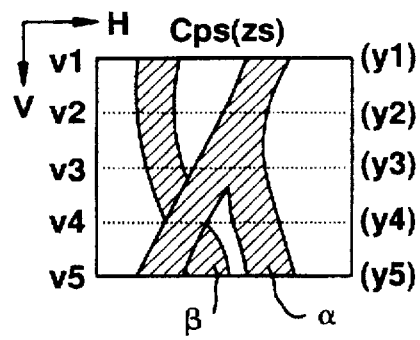

FIG. 22B shows an ultrasonic image Cps(zs) of C mode resulting from data sampling in the specified depth range. The image Cps(zs) has its horizontal direction H and vertical direction V corresponding to the x-axis direction and y-axis positions, respectively, of the scanning planes P. Specifically, the ultrasonic image Cps(zs) is a set of multiple linear images produced from image data that has first exceeded the threshold value among the PD-mode image data sampled along the scanning planes P(y1,t1)~P(y5,t5) and in the specified depth range and arrayed for display in the order of y-axis positions of the linear images. The ultrasonic image Cps(zs), which resembles a solid-geometric picture of the blood vessels α and β, exhibits the running state and narrowed portion of the blood vessels α and β.

Figure 23A:
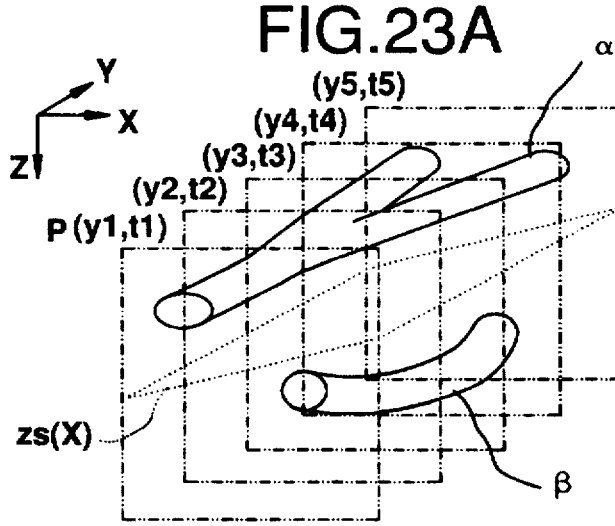
FIGS. 23A and 23B are a second set of diagrams used to explain the display of an ultrasonic image of C mode by the ultrasonic diagnostic apparatus of FIG. 21.

FIG. 23A shows the sampling of image data in PD mode along scanning planes P(y1,t1)~P(y5,t5) and in a variable depth within the range down to the variable depth specified in terms of the depth function zs(x), with the ultrasonic probe 1 being moved in the y-axis direction. The blood vessel α is included within the depth range, while the blood vessel β is not.

Figure 23B:
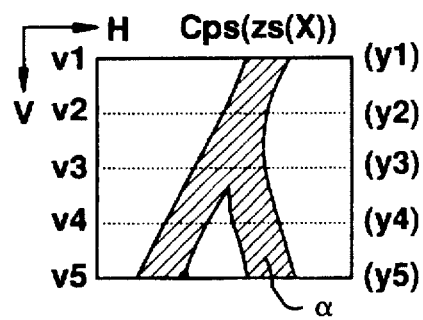

FIG. 23B shows an ultrasonic image Cps(zs(x)) of C mode resulting from data sampling in the specified depth range. The image Cps(zs(x)) has its horizontal direction H and vertical direction V corresponding to the x-axis direction and y-axis positions, respectively, of the scanning planes P. Specifically, the ultrasonic image Cps(zs(x)) is a set of multiple linear images produced from image data that has first exceeded the threshold value among the PD-mode image data sampled along the scanning planes P(y1,t1)~P(y5,t5) and in the specified depth range and arrayed for display in the order of y-axis positions of the linear images. The ultrasonic image Cps(zs), which resembles a solid-geometric picture of only the blood vessel α, exhibits the running state and narrowed portion of the blood vessel α.

The time/vertical-axis converter 60H functions to make correspondence between coordinates (h,v) of pixels of the ultrasonic image and pixel values Gps(n,y) derived from PD data that has first exceeded the threshold value among PD data Sps(n,y) sampled in a specified depth range at y-axis positions of scanning planes for sonic beams S(n) aligning in the x-axis direction.

The depth-function processor 62D functions to establish a depth function zs(x) in response to the operator's setting operation. In the case of setting only a constant depth zs without including a depth function zs(x), the depth-function processor 62D can be eliminated.

The shallowest-PD processor 64H functions to evaluate the value Sps(n,y) based on:

$$Sps(n,y)=shlw\{Spd(n,y,0)\sim Spd(n,y,zs(x)),\theta\},$$

where Spd(n,y,0)~Spd(n,y,zs(x)) represent PD data in the specified depth range of sonic beams S(n) aligning in the x-axis direction sampled at y-axis positions of scanning planes, and shlw{ } is the function of selecting PD data having shallowest value that exceeds the threshold value θ out of the contents of braces.

The ultrasonic diagnostic apparatus 700 of the foregoing seventh embodiment is capable of displaying without intermittence a C-mode ultrasonic image of even a blood vessel running in a variable depth, and capable of displaying simultaneously C-mode ultrasonic images of multiple blood vessels running in different depths.

Embodiment 8

Figure 24:
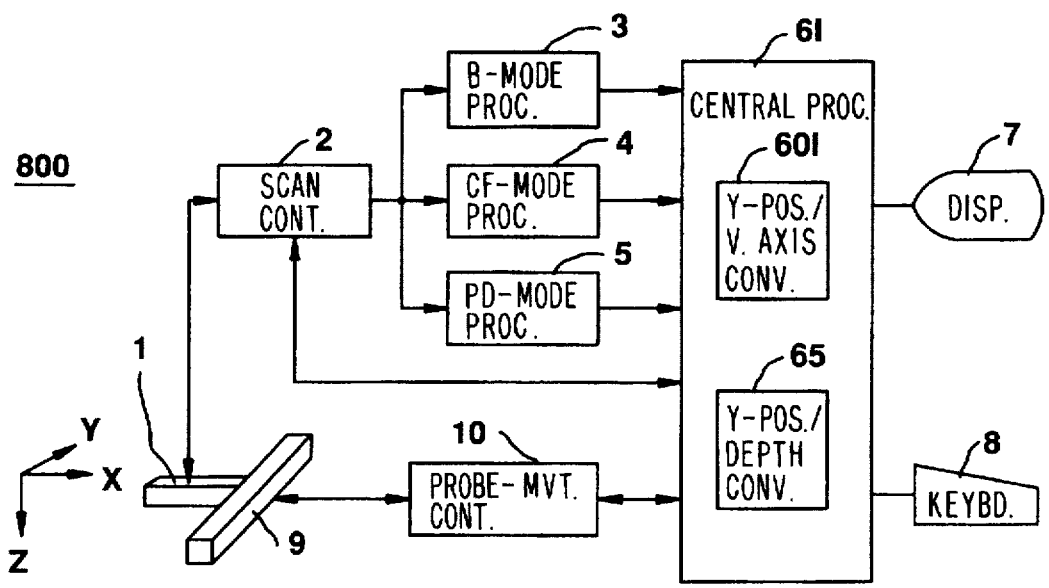
FIG. 24 is a block diagram of the ultrasonic diagnostic apparatus based on an eighth embodiment of this invention.

FIG. 24 shows in block diagram the ultrasonic diagnostic apparatus based on the eighth embodiment of this invention. The ultrasonic diagnostic apparatus 800 includes an ultrasonic probe 1 which emits ultrasonic pulses to a subject of diagnosis and receives ultrasonic echoes from the subject, a scanning controller 2 which implements the electronic scanning of the subject along a plane thereby to sample echo signals, a B-mode processor 3 which produces image data based on the magnitude of ultrasonic echoes, a CF-mode processor 4 which produces image data based on the phase of Doppler component of the echoes, a PD-mode processor 5 which produces image data based on the power of Doppler component of the echoes, a central processor 6I which produces video data from these image data, a CRT display unit 7 which displays a picture of the video data, a keyboard 8 which is used by the operator to enter instructions, a probe moving mechanism 9 which moves the ultrasonic probe 1 in the direction orthogonal to the scanning planes, and a probe movement controller 10 which controls the movement of the ultrasonic probe 1.

The central processor 6I includes a y-position/vertical-axis converter 60I and y-position/depth converter 65, which will be explained later.

The coordinate system has x axis which is the direction in which numerous sonic beams align as a result of electronical scanning, y axis which is the direction orthogonal to the scanning planes, and z axis which is the depth direction of the subject.

Figure 25A:
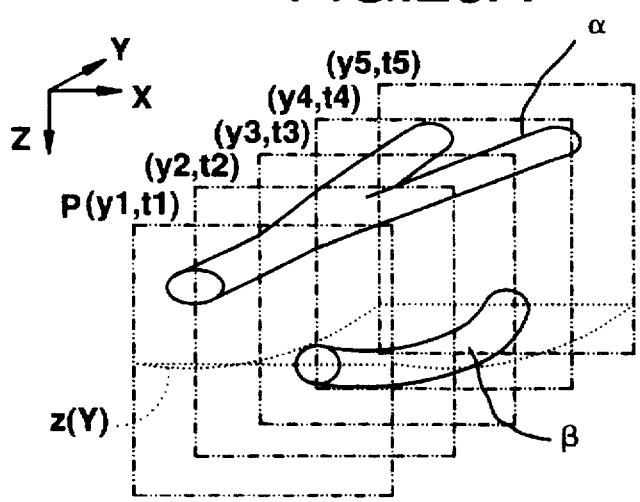
FIGS. 25A and 25B are a set of diagrams used to explain the display of an ultrasonic image of C mode by the ultrasonic diagnostic apparatus of FIG. 24.
Figure 25B:
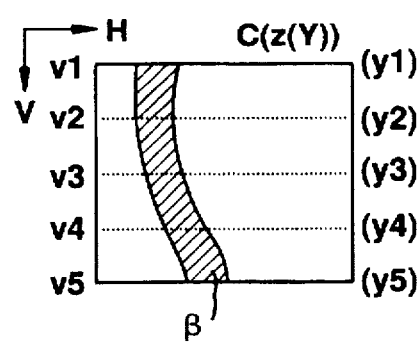

FIGS. 25A and 25B explain the display of a C-mode ultrasonic image.

The operator sets on the keyboard 8 in advance for C-mode imaging a depth function z(y) which represents a depth depending on the y-axis position.

FIG. 25A shows the sampling of image data in B mode along scanning planes P(y1,t1)~P(y5,t5) and in the variable depth specified in terms of the depth function z(y), with the ultrasonic probe 1 being moved in the y-axis direction. The blood vessel β arches downward in the section between y-axis positions y1 and y5. The depth function z(y) is set so as to follow the varying depth of the blood vessel β. Consequently, a curving plane which extends through the scanning planes P(y1,t1)~P(y5,t5) along the depth function z(y) cuts the blood vessel β in the longitudinal direction.

FIG. 25B shows an ultrasonic image C(z(y)) of C mode resulting from data sampling along the depth function z(y).

The image C(z(y)) has its horizontal direction H and vertical direction V corresponding to the x-axis direction and y-axis positions, respectively, of the scanning planes P. Specifically, the ultrasonic image C(z(y)) is a set of multiple linear images produced from B-mode image data sampled along the scanning planes P(y1,t1)~P(y5,t5) and along the depth function z(y) and arrayed for display in the order of y-axis positions of the linear images. The ultrasonic image C(z(y)), in which the blood vessel β appears to be black in the entire range, exhibits the running state and narrowed portion of the blood vessel β.

Although in the foregoing explanation, linear images are produced from B-mode image data, linear images may otherwise be produced from CF-mode image data or PD-mode image data.

The y-position/vertical-axis converter 60I functions to make correspondence between coordinates (h,v) of pixels of the ultrasonic image and pixel values Gz(y)(n,y) derived from values Sz(y)(n,y) of echo signals sampled along the depth function z(y) and at y-axis positions y of scanning planes for sonic beams S(n) aligning in the x-axis direction.

The y-position/depth converter 65 functions to establish a depth function z(y) in response to the operator's setting operation and also evaluate the Sz(y)(n,y) values of echo signals in a variable depth given by the depth function z(y).

The ultrasonic diagnostic apparatus 800 of the foregoing eighth embodiment is capable of displaying without intermittence a C-mode ultrasonic image of even a blood vessel running in a variable depth.

Variant Embodiments

The y-position/depth converter 65 explained in the foregoing eighth embodiment may be added to the ultrasonic diagnostic apparatus 500, 600 and 700 of the fifth, sixth and seventh embodiments, and in this case, these apparatus are capable of presenting a more sophisticated display of C-mode ultrasonic images of even blood vessels having complex running states.

Many widely different embodiments of the invention may be constructed without departing from the spirit and scope of the present invention. It should be understood that the present invention is not limited to the specific embodiments described in the specification, except as defined in the appended claims.

What is claimed is:

1. A method of displaying an ultrasonic image of a subject, comprising the steps of scanning the subject along a plane using an ultrasonic probe without any probe moving mechanism or controller while probing the subject within a constant depth range and using an instruction driven probe moving means while probing the subject within a variable depth range;

producing a continuous non-interrupted linear image of a portion of the subject located at a certain depth within a constant or variable depth range by using at least one of B-mode image data, CF-mode image data, and PD-mode image data resulting from the scanning, and then comparing time or position points of the used image data against vertical axis data; and displaying an array of continuous non-interrupted linear images in order of image scanning times or positions.

2. The method of claim 1, wherein the linear image is of a portion of the subject located at a constant depth.

3. The method of claim 2, wherein the producing step is repeated while moving the ultrasonic probe in a direction which is virtually orthogonal to the scanning plane and while at the same time varying the depth of imaging depending on the position of the ultrasonic probe, and then going to the displaying step.

4. The method of claim 1, wherein the linear image is of a portion of the subject located at a variable depth depending on scanning position.

5. The method of claim 1, wherein the linear image is of a portion of the subject derived from a depth wise projection of a planar image representing a portion located in a variable depth of a constant or variable range depending on scanning position.

6. The method of claim 1, wherein the linear image is obtained by converting the power level, which first exceeds a threshold value, of Doppler components of echoes which form a scanning plane, into pixel values.

7. The method of claim 1, 4, 5 or 6 wherein the producing step is repeated while moving the ultrasonic probe in a direction virtually orthogonal to the scanning plane, and then going to the displaying step.

8. The method of claim 1, wherein the linear image is derived from a depth wise projection of a planar image extracted from minimum value data along an ultrasonic beam within the depth range of the subject.

9. An apparatus for ultrasonic display, comprising:
means, comprising an ultrasonic probe, for scanning the subject along a plane using the ultrasonic probe without any probe moving mechanism or controller while probing the subject within a constant depth range and using an instruction driven probe moving means while probing the subject within a variable depth range;
means for taking the result of said means for scanning and for producing a continuous non-interrupted linear image of a portion of the subject located at a certain depth within a constant or variable depth range; and
means for displaying an array of continuous non-interrupted linear images in order of image scanning times or positions, wherein
said means for taking and producing comprises:
means for obtaining from the result of said means for scanning B-mode image data, CF-mode image data, and PD-mode image data;
means for using at least one of said B-mode image data, CF-mode image data, and PD-mode image data; and
means for comparing time or position points of the used image data against vertical axis data.

10. The apparatus of claim 9, wherein said means for producing comprises means for producing a linear image of the subject portion as it is derived from a depth-wise projection of a planar image which represents the subject portion located in a variable depth of a constant range or a variable range dependent on the scanning position.

11. The apparatus of claim 9, wherein said means for producing comprises means for producing at least one linear image which represents a subject portion located at a constant depth or a variable depth depending on the scanning position.

12. The apparatus of claim 9, wherein said means for producing comprises means for converting the power level which first exceeds a threshold value of Doppler components of echoes which form the scanning plane, into pixel values.

13. The apparatus of claim 10 or 11 further comprising means for detecting the position of the ultrasonic probe which is moved in a direction which is virtually orthogonal to the scanning plane; and wherein said means for displaying comprises means for displaying the array of linear images in order of probe position which correspond to the linear image.

14. The apparatus of claim 9, 10, 11, 12 or 13 wherein said means for producing comprises means for processing the scanning signal to vary the depth or range of depth of imaging depending on the position of the probe.

15. The apparatus of claim 9, wherein said means for producing comprises means for converting the power level, which first exceeds a threshold value, of Doppler components of echoes which form the scanning plane, into pixel values.

16. The apparatus of claim 9, wherein said means for taking and producing comprises means for deriving the linear image from a depth wise projection of a planar image extracted from minimum value data along an ultrasonic beam within the depth range of the subject.

* * * * *